US010575710B1

(12) United States Patent
Kumar et al.

(10) Patent No.: US 10,575,710 B1
(45) Date of Patent: Mar. 3, 2020

(54) SUPER ABSORBING COMPOSITE MATERIAL, FORM FACTORS CREATED THEREFROM, AND METHODS OF PRODUCTION

(71) Applicant: OCEANIT LABORATORIES, INC., Honolulu, HI (US)

(72) Inventors: Ashavani Kumar, Honolulu, HI (US); Sumil Singh Thapa, Honolulu, HI (US)

(73) Assignee: OCEANIT LABORATORIES, INC., Honolulu, HI (US)

( * ) Notice: Subject to any disclaimer, the term of this patent is extended or adjusted under 35 U.S.C. 154(b) by 849 days.

(21) Appl. No.: 14/809,090

(22) Filed: Jul. 24, 2015

Related U.S. Application Data

(60) Provisional application No. 62/031,113, filed on Jul. 30, 2014.

(51) Int. Cl.
| | |
|---|---|
| *A61F 13/53* | (2006.01) |
| *A47L 23/20* | (2006.01) |
| *A61F 13/539* | (2006.01) |
| *B32B 5/02* | (2006.01) |
| *B32B 29/02* | (2006.01) |
| *B05D 1/02* | (2006.01) |

(52) U.S. Cl.
CPC ............ *A47L 23/20* (2013.01); *A61F 13/539* (2013.01); *B05D 1/02* (2013.01); *B32B 5/022* (2013.01); *B32B 29/02* (2013.01); *A61F 2013/530226* (2013.01); *A61F 2013/530481* (2013.01); *A61F 2013/53908* (2013.01); *B32B 2264/02* (2013.01); *B32B 2307/7145* (2013.01)

(58) Field of Classification Search
CPC ...... A61F 13/15642; A61F 2013/15837; A61F 2013/15934; A61F 2013/15991; A61F 2013/530226; A61F 2013/53024; A61F 2013/53089; A61F 2013/530496; B32B 5/022; B32B 2264/02; B05D 1/02; B05D 1/06
See application file for complete search history.

(56) References Cited

U.S. PATENT DOCUMENTS

| | | | |
|---|---|---|---|
| 3,906,131 A | 9/1975 | Boe | |
| 4,074,721 A * | 2/1978 | Smits | A61F 13/141 450/37 |
| 4,459,068 A * | 7/1984 | Erickson | B32B 27/30 405/264 |
| 4,978,570 A * | 12/1990 | Heyn | A61F 13/49011 442/370 |

(Continued)

*Primary Examiner* — Catharine L Anderson
(74) *Attorney, Agent, or Firm* — Fresh IP PLC; Clifford D. Hyra; Aubrey Chen

(57) ABSTRACT

Super absorbent material used for drying that integrates super absorbent non-woven fibrous mats with other material, as for example wicking material, are described. The fibrous mats consist of polymeric material embedded with particles of super absorbent polymer. The wicking material may be lightweight knitted fabric that actively absorbs and wicks liquid across the fabric surface. The materials are fabricated as single layer or multiple layers and demonstrate a variety of form factors suitable to the intended use. The super absorbent materials may incorporate additional functionalities, such as antifungal or antibacterial, for biomedical uses.

14 Claims, 6 Drawing Sheets

(56) References Cited

U.S. PATENT DOCUMENTS

| | | | | |
|---|---|---|---|---|
| 5,399,445 A | * | 3/1995 | Tinker | H01G 9/08 |
| | | | | 429/90 |
| 5,444,871 A | * | 8/1995 | Lopez | A41D 13/1227 |
| | | | | 2/114 |
| 5,571,529 A | * | 11/1996 | Cheong | A61L 15/26 |
| | | | | 206/440 |
| 5,623,888 A | * | 4/1997 | Zafiroglu | D04H 1/52 |
| | | | | 112/414 |
| 5,651,862 A | * | 7/1997 | Anderson | A61F 13/534 |
| | | | | 162/127 |
| 6,139,912 A | * | 10/2000 | Onuschak | A61F 13/15658 |
| | | | | 222/1 |
| 6,540,853 B1 | * | 4/2003 | Suzuki | D21H 21/22 |
| | | | | 156/181 |
| 6,572,735 B1 | * | 6/2003 | Wallajapet | A61L 15/425 |
| | | | | 162/100 |
| 8,367,570 B2 | | 2/2013 | Reneker | |
| 8,454,836 B2 | | 6/2013 | Chase | |
| 2002/0102739 A1 | * | 8/2002 | Nomura | G01N 1/30 |
| | | | | 436/169 |
| 2004/0087923 A1 | * | 5/2004 | Cole | A61F 13/531 |
| | | | | 604/365 |
| 2008/0032035 A1 | | 2/2008 | Schmidt | |
| 2008/0128101 A1 | | 6/2008 | Furman | |
| 2011/0125119 A1 | * | 5/2011 | Weismantel | A61F 13/537 |
| | | | | 604/372 |

\* cited by examiner

SUPER ABSORBING COMPOSITE MATERIAL, FORM FACTORS CREATED THEREFROM, AND METHODS OF PRODUCTION

CROSS-REFERENCE TO RELATED APPLICATIONS

This application claims the benefit of U.S. provisional patent application Ser. No. 62/031,113 filed Jul. 30, 2014 by the present inventors, which provisional application is incorporated in its entirety by this reference.

STATEMENT REGARDING FEDERALLY SPONSORED RESEARCH OR DEVELOPMENT

This invention was supported in part by SBIR Contract No. M67854-14-C-6520 with the U.S. Navy. The government has certain rights in the invention.

FIELD OF THE INVENTION

The subject invention relates to materials used for drying and methods used to produce such materials. More particularly, the subject invention relates to the synthesis and integration of absorbent non-woven fibrous mats with other materials to create composite super absorbent materials and the manner of using the materials.

BACKGROUND OF THE INVENTION

Efficient drying of clothing, footwear and other items can be a significant problem particularly for those in the field. Wet clothing is uncomfortable to wear and can hinder mobility. Wet clothing and footwear are also major causes of sores, blisters, skin infections and various foot disorders. In cold weather, wet clothing increases body heat loss resulting in cold injuries such as hypothermia.

Current methods of drying clothing, footwear and other items including using newspaper and other materials as wicking, circulating hot air from blow dryers, chemical heat packs, and chemical desiccators, while sometimes available in fixed facilities, are not always accessible, may be cumbersome, and may require an available power source.

Currently available absorbent and super absorbent materials include chamois-like towels and rags made from natural or synthetic hydrophilic fibers or polyvinyl (PVA) or polyacrylate foams. Other known and commercially available absorbents include materials impregnated with pockets of super absorbing polymers, materials mixed with super absorbing polymers during fabrication, and materials adhered/coated with a film of super absorbing polymer.

Some of these prior art materials are described in U.S. Pat. No. 3,906,131 A to Boe, a chamois leather-like material having improved water absorbency and abrasion resistance; US 20080128101 A1 of Furman, teaching a method of applying a super-absorbent composition to tissue or towel substrates; US 20080032035 A1 of Schmidt, disclosing an absorbent structure with improved water-absorbing material; U.S. Pat. No. 8,367,570 B2 to Renecker, describing a mechanically strong absorbent non-woven fibrous mats; and U.S. Pat. No. 8,454,836 B2 to Chase, disclosing a method for removing water from an organic liquid.

State of the art towels that employ the technologies described above have limited absorption capacity. The invention disclosed below and in the accompanying figures significantly improves absorptive capacity by, among other things, the incorporation of super absorbing polymers into mat composite materials and form factors.

Current applications of super absorbing polymers have significant limitations due to difficulty of use, which stem from form factors. The disclosed invention creates a novel material by changing the form factor of the integrated super absorbing polymers that increase ease of use as well as performance in a variety of drying applications.

The new super absorbent materials disclosed herein may also include antimicrobial properties and other functionalities not present in the prior art absorbents, and can be used for biomedical applications.

SUMMARY AND PREFERRED EMBODIMENTS

The subject invention is super absorbent composite materials that integrate absorbent non-woven fibrous mats, or powders or films, with other material, as for example wicking material. The invention also relates to the bilayer and multilayer structures of such materials that facilitates or are required to achieve efficient drying.

The subject invention is the method of making super absorbent composite materials that integrate absorbent non-woven fibrous mats, or powders or films with other material, as for example wicking material.

The subject invention may include additional unique features such as antimicrobial activity incorporated into the super absorbent non-woven fibrous mats.

One aspect of the subject invention is super absorbing composite materials comprising an absorbent non-woven fibrous mat or other absorbent material produced directly onto a wicking material for the purpose of producing a drying material.

A further aspect of the subject invention is the typical architectures for such materials which include super absorbent non-woven fibrous mats sandwiched between two layer of moisture wicking cloth/materials, or a moisture wicking cloth sandwiched between layers of super absorbing polymer fiber mat, or a bilayer of moisture wicking cloth and absorbent non-woven fibrous mats.

Another aspect of the subject invention is form factors produced from the subject invention that increase the ease of use as well as performance in drying applications, as for example, the super absorbent composite formed into a drying towel, boot liner, sock, diaper or undergarment.

A further aspect of the subject inventions is methods for producing such super absorbent composite materials.

Drying can be defined as the removal of a liquid such as water from another material, surface, or another liquid.

The drying materials of the subject invention can be used for the removal of a liquid such as water from another material, a surface, or another liquid. So, for example, the super absorbing composite material of the disclosed invention can be used to remove moisture from petrochemicals, fuels and other materials, in the manufacture of clothing, and in many other manners and form factors.

DETAILED DESCRIPTION OF PREFERRED EMBODIMENTS

Super Absorbing Composite Materials

Figure 1A:
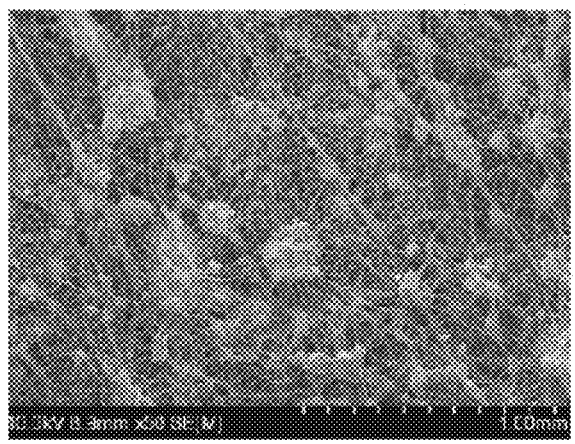
FIG. 1A is a micrograph of a super absorbent non-woven fibrous mat of the subject invention before wetting.

The super absorbing composite material of the present invention comprises an absorbent non-woven fibrous mat and a wicking material.

The absorbent non-woven fibrous mat is made of fibers, powders or films consisting of a polymeric material embedded with particles of super absorbent polymer. The polymeric material includes, but is not limited to, polycaprolactone, polylactic acid, cellulose, polyvinyl alcohol, polyethylene oxide, nylon, polyester, polyacrylic acid, polyacrylic amide, polyurethane, polyvinyl chloride, other polymer or copolymer and/or their blend mixture. The super absorbing polymer particles include, but are not limited to, polyacrylate or polyacrylamide copolymer of polyacrylamide, ethylene maleic anhydride, cross-linked carboxymethylcellulose, polyvinyl alcohol, cross-linked polyethylene oxide, or starch grafted copolymer of polyacrylonitrile.

The liquid trapping, absorbent non-woven fibrous mat improves the feel of the material when wet, such that the material surface feels dry and cool.

An example of wicking material for use in the super absorbent composite is lightweight knitted fabric that actively absorbs and wicks liquid across the fabric surface. Any wicking material such as cloth, paper or sheet can be used in this technology. Examples of commercially available wicking materials suitable for use in the invention include Drirelease, DRY INSIDE, Coolmax and 100% cotton fabric.

The wicking material spreads liquid across the material which allows transfers of the liquid to the super absorbent non-woven fibrous mat. The fibrous mat has the potential to absorb and trap up to 1000 times its weight in liquid. The combined effect of wicking, absorption, and trapping increases the drying performance. The incorporation of wicking material improves mechanical properties of the non-woven fibrous mat, increasing thereby the range of applications and ease of use of the composite material.

According to certain preferred embodiments, multifunctional properties may be incorporated into the super absorbent materials including, without limitation, anti-bacterial/fungal properties, odor-reducing properties, reusability properties, and biodegradability properties.

For example, the absorbent non-woven fibrous mats of the subject invention may be impregnated with antibacterial agents. Such antibacterial agents include, but are not limited to heavy metals and their alloys including silver and silver salts (silver nitrate, silver chloride, silver benzoate), copper and copper salts; and zinc and zinc salts; anti-microbial plant extracts such as thymol from natural sources such as thyme, rosemary, hibiscus, coffee plants and their synthetic equivalents (basic phenolic compounds); proprietary agents available commercially to impart antifungal, antiviral, and/or anti-bacterial properties into textiles; dehydrating and fixative agents such as alcohols and aldehydes; oxidizing agents such as hypochlorites; quanternary ammonium compounds such as benzalkonium chloride; and halogenated tertiary amines. These or other antibacterial agents can be added to the super absorbent composite to inhibit microbial/fungal growth.

The super absorbent composite material can be used directly as a single layer or as a multi-layer material in its applications. Typical architectures for the multi-layer material include (1) absorbent non-woven fibrous mats sandwiched between two layer of moisture wicking cloth/materials; (2) a moisture wicking cloth sandwiched between layers of super absorbing polymer fiber mat; or (3) a bi-layer of moisture wicking cloth and absorbent non-woven fibrous mats. Other architectures for the super absorbent composite material may be employed without departing from the scope of the subject invention.

Figure 1B:
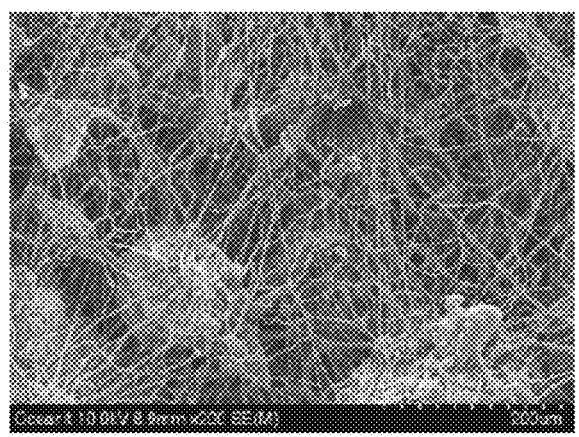
FIG. 1B is a micrograph of a super absorbent non-woven fibrous mat of the subject invention after wetting.

Illustrated in FIG. 1A is the microstructure of a preferred embodiment of a super absorbent non-woven fibrous mat material 150 before wetting. FIG. 1B shows the microstructure of the same preferred embodiment of the non-woven fibrous mat material 150 after wetting.

Figure 2:
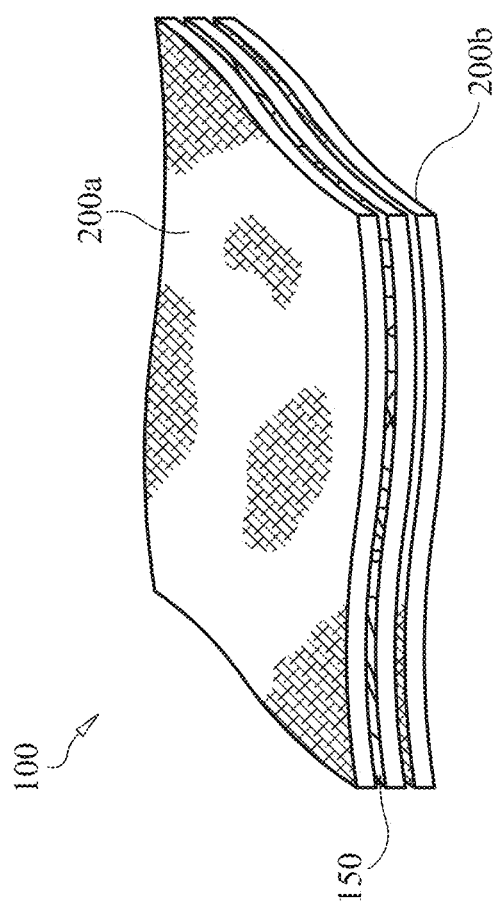
FIG. 2 is an exploded perspective view of a preferred embodiment of a typical architecture of the super absorbent composite material of the subject invention.
Figure 2:
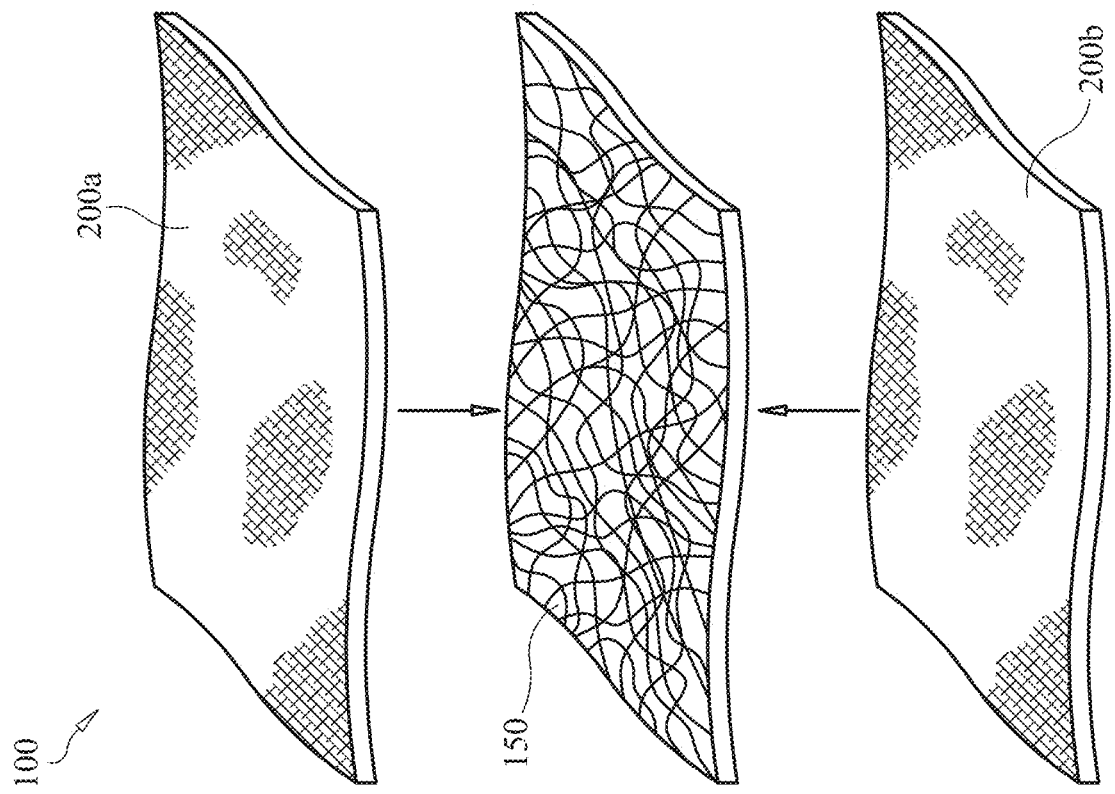

Depicted in FIG. 2 is one preferred embodiment of a multilayered architecture of a super absorbent composite material 100 of the subject invention in exploded view. A super absorbent non-woven fibrous mat 150, comprising the inside layer of the multi-layer drying material 100 is sandwiched between two layers 200a and 200b of moisture wicking material, creating a towel-like composite fabric. By way of example and not limitation, Drirelease fabric may be selected for moisture wicking material layers 200a and 200b because it employs specifically engineered polyester fibers to improve "breathability" as well as a high moisture wicking rate compared to natural fibers such as cotton. The towel-like dual layer system illustrated in FIG. 2 has the tactile benefits of the moisture wicking material on both outside surfaces, while still retaining drying performance.

Form Factors to Dry Boots and Garments

The towel-like dual layer system illustrated in FIG. 2 can be used as a drying fabric to dry garments and other articles of clothing. According to a preferred embodiment, dimensions of the towel-like dual layer system to accommodate the length and width of a medium-size adult garment are approximately 28"×24".

Figure 3A:
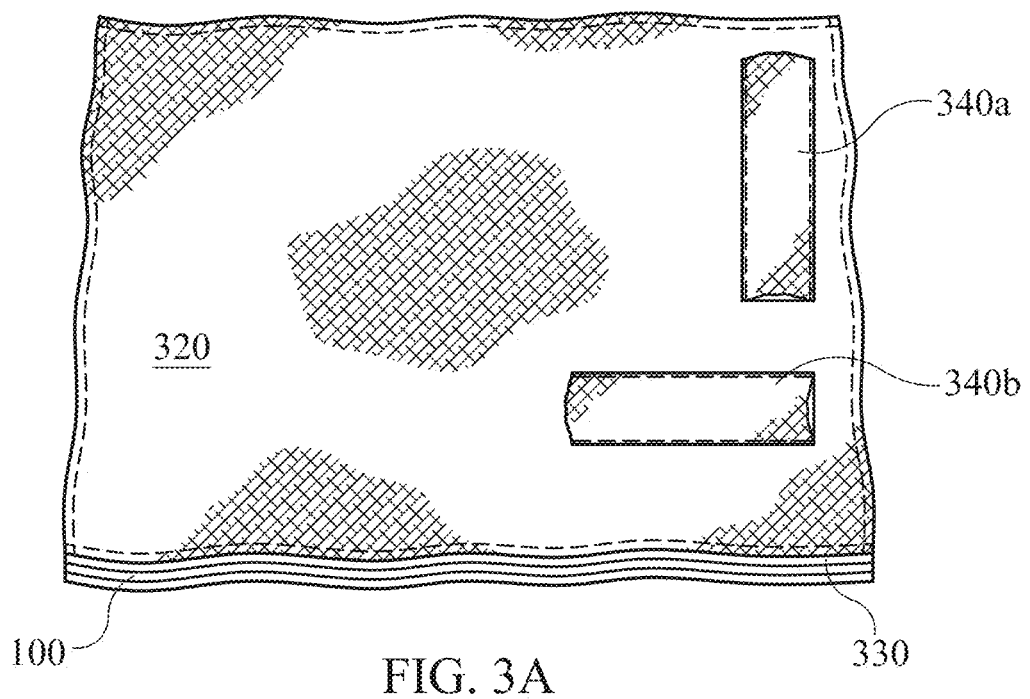
FIG. 3A is a perspective view showing a form for drying a boot utilizing the subject invention.
Figure 3B:
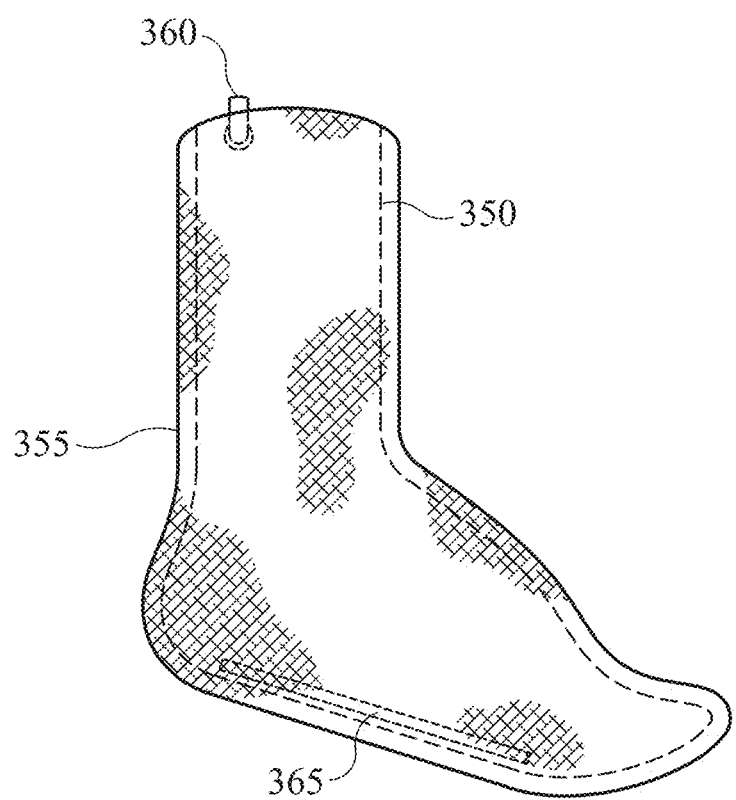
FIG. 3B is a perspective view showing an alternate form for drying a boot utilizing the subject invention.

In addition, the subject invention can be used to create novel form factors that increase the ease of use as well as the performance in drying applications. FIGS. 3A through 3B illustrate the super absorbent composite material in a towel and inflatable sock form, respectively, being used to dry a boot. A medium weight towel 320 depicted in FIG. 3A consists of layers of the super absorbent composite material 100 and a batting filler type material 330, such as a terry cloth, sewn together. The terry cloth serves to add volume to the towel making it thick enough to use rolled up, to reduce the overall weight of the towel and the amount of super composite material needed, as well as to allow the towel to be used for personal drying. The towel illustrated contains two pockets, 340a and 340b, positioned perpendicular to one another to receive a small rod to make boot insertion easier. According to a preferred embodiment, the towel dimensions are approximately 16" by 22", chosen based on measurements of length and height of a size 11 boot.

The inflatable sock illustrated in FIG. 3B is constructed of two layers, an inner inflatable bladder 350 and an outer layer 355 comprising the super absorbent composite material of the subject invention. Inflatable bladder 350 is made from rubberizing a cotton cloth to make airtight and grafting a plastic inflation valve 360 to the top for easy inflation and deflation. Inflation valve 360 is a one way valve until squeezed so that air does not escape while capping with plug. Inflatable bladder 350 also incorporates a stiff rod 365 along the length of the sole to make insertion easier. The super absorbent composite material layer 355 is shaped to fit the interior of the boot. The design is intended to be easily rolled along the length of the sole for easy packing. In a typical process, the inflatable towel can be inserted easily into the boot and inflated by mouth to initiate contact with inner boot surface. Removal consists of unplugging the inflation valve to allow the compressed air to escape, pulling the device out of boot, and rolling up the device with the valve squeezed for tight packing.

Other Form Factors

The super absorbent composite of the described invention and the layered architecture illustrated in FIG. 2 may be used in a number of other form factors including, without limitation, sponge, chamois, super absorbent reusable and disposable diapers, super absorbent reusable and disposable undergarments, and sports and performance garments to name a few. The composite material efficiently removes sweat and other bodily fluids from the body leaving the inner and other surfaces of the composite cool and dry.

Methods for Making Super Absorbent Composite Materials

Methods of fabricating the super absorbent composite material of the subject invention include the following: Super absorbing polymer particles (that include but are not limited to, polyacrylate or polyacrylamide, copolymer of polyacrylamide, ethylene maleic anhydride, cross-linked carboxymethylcellulose, polyvinyl alcohol, cross-linked polyethylene oxide, or starch grafted copolymer of polyacrylonitrile) are suspended in a liquid/solution of polymeric material (that include but are not limited to, polycaprolactone, polylactic acid, cellulose, polyvinyl alcohol, polyethylene oxide, nylon, polyester, polyacrylic acid, polyacrylic amide, polyurethane, polyvinyl chloride and their copolymer and/or their blend mixture) and formed into nano- to micro-scale fibers directly on wicking fabric, creating a non-woven fibrous mat on the surface of the wicking material. The process of fabrication of super absorbent composite materials can be carried out in a solvent such as dimethyl formamyde (DMF), hexane, alcohols, acetone, ketones, aldehydes, etc., or their combination.

Formation of fibers can be done by a range of processes known in prior art including, but not limited to, electrospinning, melt spinning, wet spinning, film adhesion, extrusion and nano-fiber by gas jet method.

For example, the mat may be fabricated incorporating the super absorbing polymer into electro-spun nanofiber. The super absorbing polymer cannot be spun directly into a nano-fiber, however, due to insolubility in non-polar solvents and a high swelling factor in polar solvents. In order to fabricate a fiber, the super absorbing polymer is electro-spun together with a suitable matrix. Polycaprolactone and polylactic acid are examples of suitable polymer matrix for the nanofiber known to electrospun into high quality fibers and are compatible with super absorbing polymer as well as many solvents.

The wicking material can be used with and without modification. Alternatively, the wicking material can be coated with adhesive, bonding agent, or the like prior to formation of the fibers in order to improve coupling of the fibrous mat with the wicking material.

The present invention also anticipates that the composite material can be directly used as a single layer or as a multi-layer material in its applications. For example, in a multi-layer application, two layers of the composite can be joined together by various means such as, but not limited to, stitching, adhesion, and hot pressing, with the super-absorbent non-woven fibrous mat sides in contact and the moisture wicking material exposed on both sides, creating a towel-like composite fabric.

EXAMPLES

Fabrication by Electrospinning

In one experiment, nanofiber mats were directly electrospun on to the moisture wicking cloth such as Drirelease fabric. According to a typical process, the Dririelease fabric was placed over the aluminum foil on the collection mandrel ~7 cm from the needle tip. A 5 mL syringe tipped with an 18-gauge needle was used to electro-spin the polymer suspension onto the fabric. The potential applied across syringe needle and aluminum foil backing was varied between 10-23 kV.

In a typical process to create the polymer suspension, a stock solution of 15% w/v polycaprolactone in a 1:1 solvent of DMF and acetone was prepared using sonication. The appropriate amount of super absorbing polymer particles was then dispersed in the stock solution to obtain the desired super absorbing polymer to polycaprolactone ratio. The polymer suspension was fed at a 15 ml/hour rate with a total of ~20 mL being used. The resulting nanofiber coated Drirelease fabric was found to be flexible and mechanically robust with good adhesion.

A computer-controlled linear actuator can be incorporated to allow continuous rastering across larger sized samples and for providing an even distribution of nanofiber across the length of the sample.

In addition, the discharging needle tip can be isolated from the syringe pump using PTFE tubing and ventilation can be added to the system to accommodate higher amounts of evaporated solvents.

Fabrication by Film Adhesion

In another experiment, a solid film of super absorbent polymer was fabricated separately on polyethylene foil by spray coating followed by partial curing at 120 degrees Celsius. The film was transferred onto the wicking material by cold pressing under wet conditions. The film behaved as glue, adhering well to the wicking material's surface.

Anti-Bacterial/Fungal Study

Studies on the effectiveness of silver benzoate incorporated into the absorbent non-woven fibrous mats of the subject invention to inhibit microbial/fungal growth were performed as a precursor to using actual silver nanoparticles or other particles in the invention. Silver nanoparticles are already used in other clothing for their antimicrobial property and are commercially available.

Formulations were tested with varying amounts of silver benzoate by percentage weight added to the polymer suspension. An example of one such formulation comprised a solution of polycaprolactone, super absorbing polymer, and silver benzoate of 25%, 74.75%, and 0.25% by weight, respectively.

Nanofiber mats were directly electro-spun onto the moisture wicking fabric placed over aluminum foil on the collection plate ~7 cm from the needle tip. A 5 mL syringe tipped with a 16-gauge needle was used to electro-spin a polymer suspension with silver benzoate onto the fabric, while the electrical potential applied across the syringe needle and aluminum foil backing is varied between 10-30 kV. The polymer suspension with silver benzoate is fed at 0.25 mL/min with a total of ~20 mL being used. After electro-spinning, the silver benzoate is reduced to nanoparticles by exposing the specimen to ultraviolet light.

Antimicrobial activity of these formulations was observed and measured by employing the AATCC 147 test method. This uses streaks of bacteria to indicate antimicrobial activity and determines the sensitivity of facultative aerobic bacteria to various antimicrobial compounds or materials. The presence or absence of growth around disks or swatches of fabric are an indirect measure of the ability of that compound to inhibit replication in the selected microbe.

In this analysis, *Staphylococcus aureus* (*S. aureus*, bioMerieux catalog number 56009) and *Escherichia coli* (*E. coli*, bioMerieux catalog number 56006) were selected as these microbes normally colonize human skin surfaces. These microbes were purchased and sample bacteria stocks were tested for common antibiotic resistance, including penicillin, streptomycin, and gentamycin, prior to experiments for antimicrobial activity for this project (data not shown).

Positive controls using appropriate antibiotics were included in all tests. The moisture wicking fabric was tested separately from the nanofiber mat in order to determine the isolated effect of each material.

The continuity of the bacterial streaks indicated that neither the moisture wicking fabric nor the invention by themselves has anti-microbial/fungal activity, but that the invention incorporating silver benzoate demonstrated gaps in the streaks due to interrupted growth of bacteria. As such, the antimicrobial property of the present invention offers biomedical applications.

Drying Performance of the Invention

Figure 4A:
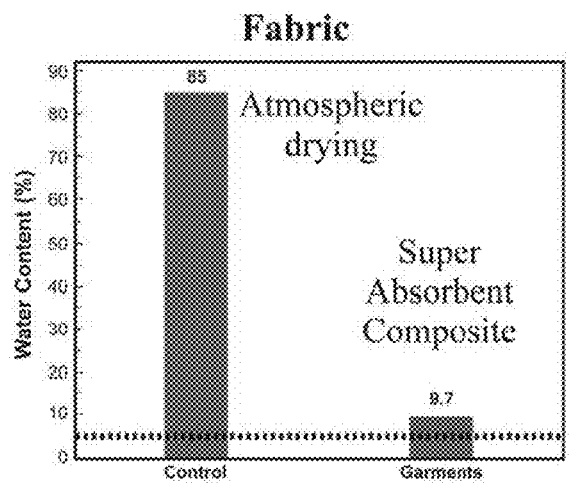
FIG. 4A is a bar graph illustrating the water content of fabric garment dried using the subject invention versus atmospheric drying.
Figure 4B:
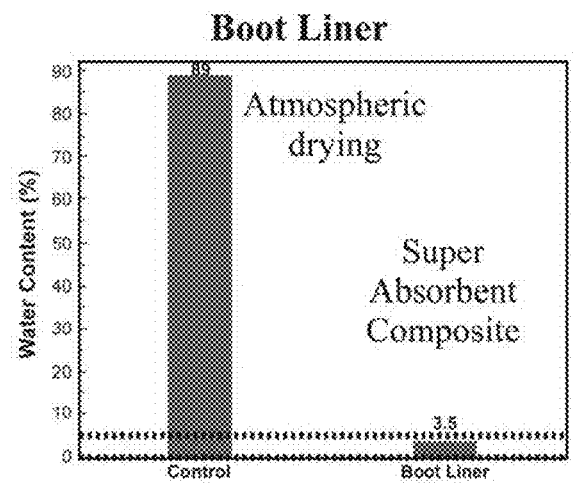
FIG. 4B is a bar graph illustrating the water content of a boot liner dried using the subject invention versus atmospheric drying.

The drying performance of the subject invention made with a super absorbing polymer to polycaprolactone ratio of 4:1 and Drirelease fabric, on normal fabric and Gore-Tex boot liner is illustrated in FIG. 4. The bar graph in FIG. 4A shows the water content of fabric garment dried using the subject invention versus atmospheric drying. The bar graph in FIG. 4B shows the water content of a boot liner dried using the subject invention versus atmospheric drying.

The drying performance is represented by the amount of water retained in the specimen after six hours in 65% relative humidity at 21° C. This performance was compared by line drying or atmosphere drying carried out by leaving the wetted sample in the specified condition. The water content retained was found to be 85% and 89% of the original water in the fabric specimen and Gore-Tex boot liner specimen after six hours in normal atmospheric, while the fabric and Gore-Tex boot liner show only ~9.7 and 3.5%, respectively, water content retained after treating with the invention. The higher water content retained in the specimens without treatment by the subject invention represents poor drying performance. The low water content retained in the specimens using invention as compared to atmospheric drying indicates the better drying performance achieved with application of the invented materials.

Figure 5A:
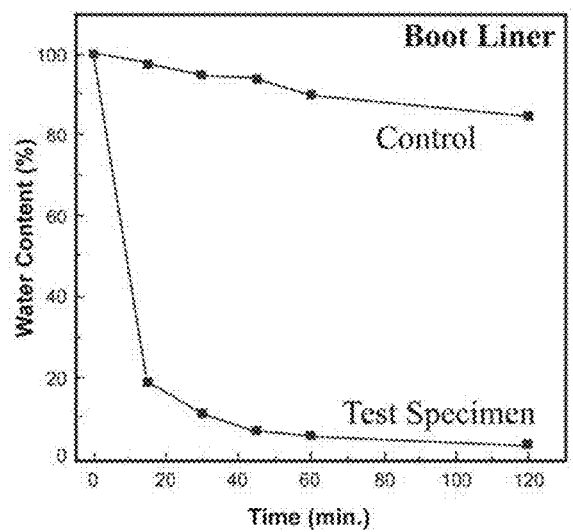
FIG. 5A is a line graph of water content of a boot liner over time where the boot liner is dried using atmospheric drying and the subject invention.
Figure 5B:
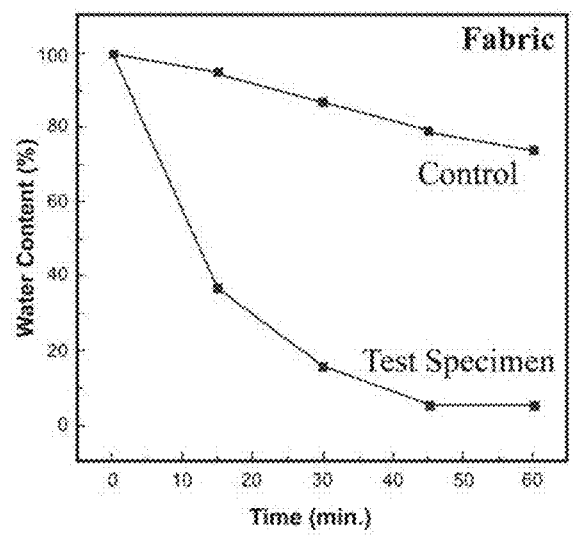
FIG. 5B is a line graph of water content of a garment over time where the garment is dried using atmospheric drying and the subject invention.

Water content of the treated fabric and boot liner samples was monitored as a function of time as illustrated in FIG. 5. The line graph in FIG. 5A shows the water content of a boot liner over time where the boot liner is dried using atmospheric drying compared with drying using the subject invention. The line graph in FIG. 5B shows the water content of a garment over time where the garment is dried using atmospheric drying compared with drying using the subject invention. The kinetic behavior for both specimens was found to be approximately exponential indicating a diffusion-based behavior for drying.

Figure 6:
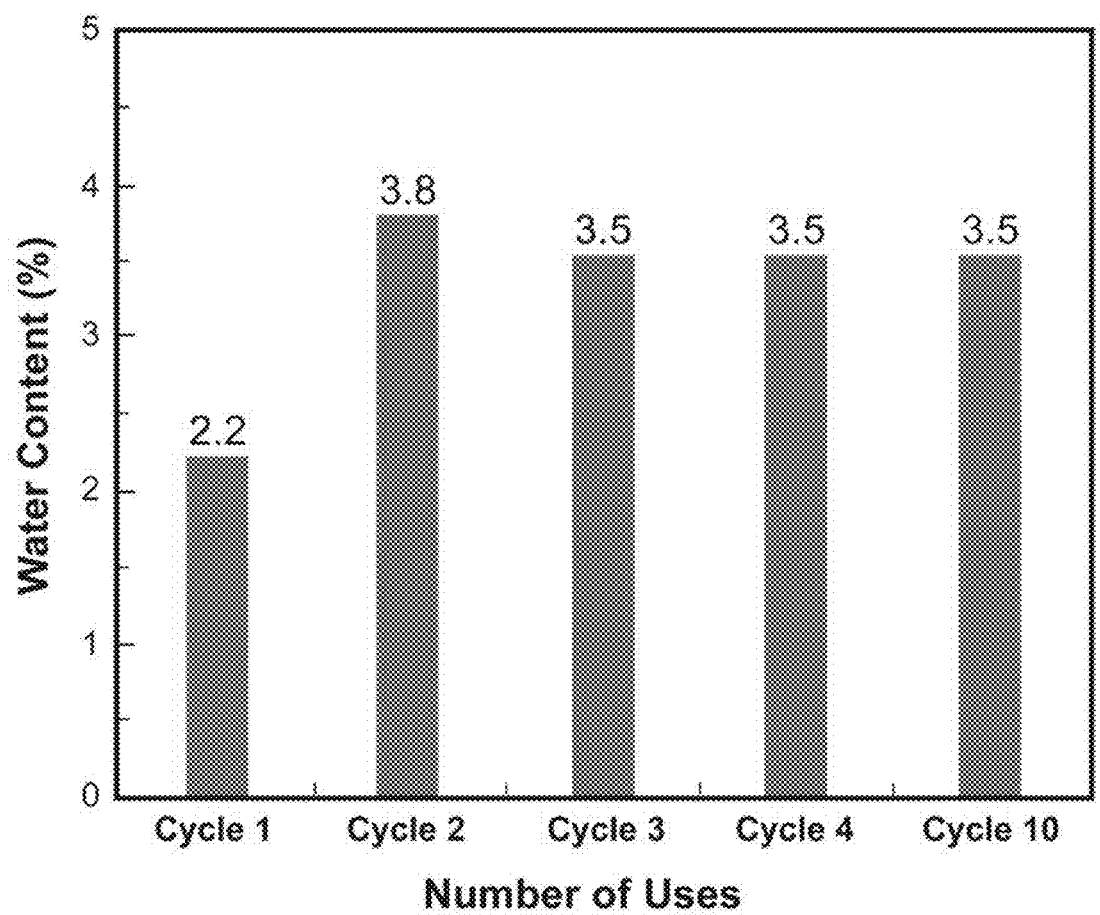
FIG. 6 is a bar graph of the water content of a boot liner after repeated use of the subject invention.

The reliability of the invention under repeated use was evaluated on boot liner specimens using the described protocol over numerous cycles. The drying performance was measured for each cycle and is summarized in the graph depicted in FIG. 6, a bar graph of the water content of a boot liner under repeated use of the subject invention. No significant change in drying performance after repeated use was observed, demonstrating high reusability.

SUMMARY AND SCOPE

As will be appreciated from the description, drawings and examples set forth above and referenced herein, the new super absorbent composite material of the subject invention provide faster, more efficient drying of clothing, footwear and other moist items compared with currently available absorbing and drying agents and methods. The composite material of the subject invention is easy and inexpensive to manufacture, can be used without power or chemicals, is easily transported, and may be made conveniently available to users in a variety of locations and environments.

Because the surface of the composite material feels dry and cool when wet, the material is particularly useful in performance wear and accessories designed for personal comfort.

The subject invention also has value as a drying fabric that can be manufactured into various form factors. More specifically, the super absorbent material can be used to make super absorbing towels. With its enhanced drying ability, such towels can be used for accelerated drying of garments and shoes wet with water. In addition, the super absorbent towels can be used in a fashion similar to a traditional towel for drying surfaces and materials, sponges, chamois, and in the manufacturing of diapers, undergarments, and performance wear.

The key to the subject invention is single layer or multilayer fabric with unique super absorbing property due to its composition and multilayer design as well as process of fabrication.

The superabsorbent composite may be formulated with antibacterial agents including silver nanoparticles, as well as other agents, to address fungus, bacteria and odors in the materials being dried or worn.

The super absorbent material of the subject invention may be fabricated to incorporate additional functionalities such as reusability and biodegradable functionalities.

The novel composite materials of the present invention have been shown to extract 90% of absorbed water from footwear and clothing in typical ambient environments, including humid environments, and may be manufactured in a variety of form factors depending upon the needs and desired uses.

While the invention has been described with reference to specific embodiments, modifications and variations of the invention may be constructed and employed without departing from the scope of the invention.

By way of example and not limitation, the material of the subject invention can be used in the fabrication of sports-wear, as for example as ski socks, for rapid drying during and after use. The material is also useful to remove moisture from liquids.

Further, the invention should be considered as comprising all possible combinations of every feature described in the instant specification, appended claims, and/or drawing figures which may be considered new, inventive and industrially applicable.

Multiple variations and modifications are possible in the embodiments of the invention described here. Although certain illustrative embodiments of the invention have been shown and described here, a wide range of modifications, changes and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features.

Accordingly, it is appropriate that the foregoing description be construed broadly and understood as being given by way of illustration and example only, the spirit and scope of the invention being limited only by the claims which ultimately issue.

The invention claimed is:

1. A method for creating a super absorbing composite material comprising the steps of:
   (a) suspending super absorbing polymer particles within a solution of polymeric material;
   (b) applying said solution to the surface of a wicking material to form a super absorbing composite material with nano- to micro-sized fibers; and
   (c) adhering two or more layers of the super absorbing composite material together,
   wherein the polymeric material is polycaprolactone, and wherein a ratio of the polymer particles to polycaprolactone is 4 to 1.

2. The method of claim 1, wherein the super absorbing polymer particles are selected from a group consisting of polyacrylate, a polyacrylamide copolymer of polyacrylamide, ethylene maleic anhydride, cross-linked carboxymethylcellulose, polyvinyl alcohol, cross-linked polyethylene oxide, a starch grafted copolymer of polyacrylonitrile, and any combination thereof.

3. The method of claim 1, wherein the polymeric material is selected from a group consisting of polycaprolactone, polylactic acid, cellulose, polyvinyl alcohol, polyethylene oxide, nylon, polyester, polyacrylic acid, polyacrylic amide, polyurethane, polyvinyl chloride and their copolymers, and any combination thereof.

4. The method of claim 1, wherein a solvent for dissolving the polymeric material is selected from a group consisting of DMF, hexane, alcohols, ketones, aldehydes, and any combination thereof.

5. The method of claim 1, wherein the mechanism for applying said solution to the surface of wicking material is selected from a group consisting of extrusion, spraying, cold pressing under wet conditions, electrospinning, melt spinning, film adhesion, extrusion, and gas jet.

6. The method of claim 1, comprising the further step of coating the wicking material with a bonding agent prior to applying solution containing super absorbing polymer particles to said wicking material.

7. The method of claim 1, comprising the further step of applying an anti-microbial agent to the resulting composite material.

8. The method of claim 7, wherein the anti-microbial agent is selected from a group consisting of heavy metals and their alloys; anti-microbial plant extracts; antifungal and/or antiviral agents; dehydrating and fixative agents; oxidizing agents; quaternary ammonium compounds; and halogenated tertiary amines.

9. A method for creating a super absorbing composite material, the method comprising:
   suspending a plurality of super absorbing polymer particles in a solution of polymeric material, thereby generating a suspended solution;
   applying the suspended solution to a surface of a wicking material; and
   forming the super absorbing polymer particles in the suspended solution into nano-scale to micro-scale fibers directly on the surface, thereby generating a super absorbing composite material,
   wherein the forming step comprises electrospinning.

10. A method for creating a super absorbing composite material comprising the steps of:
    (a) suspending super absorbing polymer particles within a solution of polycaprolactone; and
    (b) applying said solution to the surface of a wicking material to form super absorbing nano- to micro-sized fibers,
    wherein a ratio of the polymer particles to polycaprolactone is 4 to 1.

11. The method of claim 10, wherein the super absorbing polymer particles are selected from a group consisting of polyacrylate, a polyacrylamide copolymer of polyacrylamide, ethylene maleic anhydride, cross-linked carboxymethylcellulose, polyvinyl alcohol, cross-linked polyethylene oxide, a starch grafted copolymer of polyacrylonitrile, and any combination thereof.

12. The method of claim 10, wherein a solvent for dissolving the polycaprolactone is selected from a group consisting of DMF, hexane, alcohols, ketones, aldehydes, and any combination thereof.

13. The method of claim 10, wherein the mechanism for applying said solution to the surface of wicking material is selected from a group consisting of extrusion, spraying, cold pressing under wet conditions, electrospinning, melt spinning, film adhesion, extrusion, and gas jet.

14. The method of claim 10, comprising the further step of coating the wicking material with a bonding agent prior to applying solution containing super absorbing polymer particles to said wicking material.

* * * * *